United States Patent
Killmann

Patent Number: 5,846,198
Date of Patent: Dec. 8, 1998

[54] APPARATUS FOR LOCALIZING ACTION CURRENTS IN THE HEART

[75] Inventor: Reinmar Killmann, Forchheim, Germany

[73] Assignee: Siemens Aktiengesellschaft, Munich, Germany

[21] Appl. No.: 866,421

[22] Filed: May 30, 1997

[30] Foreign Application Priority Data

May 31, 1996 [DE] Germany ............ 196 22 078.5

[51] Int. Cl.⁶ .................................................. A61B 5/02
[52] U.S. Cl. ................. 600/424; 600/382; 600/508; 600/450
[58] Field of Search ................... 600/382, 424, 600/508, 447, 450

[56] References Cited

U.S. PATENT DOCUMENTS

| | | | |
|---|---|---|---|
| 3,744,479 | 7/1973 | Stein et al. | 128/2 S |
| 4,173,228 | 11/1979 | Van Steenwyk et al. | 128/653 |
| 4,905,698 | 3/1990 | Strohl et al. | 128/653 |
| 5,078,678 | 1/1992 | Katims | 604/28 |
| 5,295,486 | 3/1994 | Wollschläger et al. . | |
| 5,311,873 | 5/1994 | Savard et al. | 128/696 |
| 5,391,199 | 2/1995 | Ben-Haim . | |
| 5,398,691 | 3/1995 | Martin et al. | 128/662.06 |

FOREIGN PATENT DOCUMENTS

| | | |
|---|---|---|
| 32 11 003 | 6/1984 | Germany . |
| 40 37 586 | 5/1992 | Germany . |
| 43 06 037 | 9/1994 | Germany . |
| 44 18 868 | 5/1995 | Germany . |

OTHER PUBLICATIONS

"Endocardial Catheter Mapping: Validation of a Cineradiographic Method For Accurate Localization of Left Ventricular Sites," Hauer et al, Circulation, vol. 74, No. 4, Oct. 1986, pp. 862–868.

"The Influence of Inhomogeneous Volume Conductor Models on the ECG and the MCG," Bruder et al, Phys. Med. Biol. vol. 30 (1994), pp. 1949–1968.

"Radiofrequency Catheter Ablation Guided By Intracardiac Echocardiography," Chu et al, Circulation, vol. 89, No. 3, Mar. 1994, pp. 1301–1305.

"Body Surface Isopotential Mapping of the Entire QRST Complex in the Wolff–Parkinson–White Syndrome. Correlation With the Location of the Accessory Pathway," Giorgi et al, American Heart Journal, vol. 121, No. 5, May 1991, pp. 1445–1453.

"Transesophageal Echocardiography during Radiofrequency Caatheter Ablation of Ventricular Tachycardia," Saxon et al, The American Journal Of Cardiology, vol. 72, Sep. 15, 1993, pp. 658–661.

"Probability Based Dipole Localization and Individual Localization Error Calculation In Biomagnetism," Scholz et al, Proc. 14th Ann. Int. Conf. IEEE Eng. Med. Biol. Soc., Paris 1992, pp. 1766–1767.

(List continued on next page.)

*Primary Examiner*—Marvin M. Lateef
*Assistant Examiner*—Eleni Mantis Mercader
*Attorney, Agent, or Firm*—Hill & Simpson

[57] ABSTRACT

An apparatus for localizing action currents in the heart of a living subject has electrodes for acquiring a distribution of electrical potential on the body surface of the living subject generated by the action currents, a position acquisition unit for determining the spatial position of the electrodes, and a localization unit connected to the electrodes and to the position acquisition unit. The localization unit localizing the action currents from the distribution of potential and the spatial position of the electrodes. A reference catheter fixable in the heart is fashioned such that its spatial position can be determined by the position acquisition unit, and that the localization unit localizes the action currents with reference to the reference catheter.

10 Claims, 2 Drawing Sheets

OTHER PUBLICATIONS

"Body Surface Mapping of Ectopic Left and Right Ventricular Activation, QRS Spectrum in Patients Without Structural Heart Disease," SippensGroenewegen et al, Circulation, vol. 82, No. 3, Sep. 1990, pp. 879–896.

"Potential Applications of Intracardiac Echocardiography in Interventional Electrophysiology," Tardif et al, American Heart Journal, vol. 127, No. 4, Part II, Apr. 1994, pp. 1090–1094.

APPARATUS FOR LOCALIZING ACTION CURRENTS IN THE HEART

BACKGROUND OF THE INVENTION

1. Field of the Invention

The present invention is directed to an apparatus for localizing action currents in the heart of a living subject, of the type having electrodes for acquiring a distribution of electrical potential on the body surface of the subject generated by the action currents, a position acquisition unit for determining the spatial position of the electrodes, and a localization unit connected to the electrodes and to the position acquisition unit, the localization unit localizing the action currents from the distribution of potential and the spatial position of the electrodes.

2. Description of the Prior Art

Heart rhythm disturbances represent a significant group of ailments in cardiology. A clinically practiced therapy of heart rhythm disturbances is ablation of the arrhythmogenic tissue in the heart. To that end, an ablation catheter is introduced via a vein or an artery into the atrium or the ventricle of the heart. In the heart, the location that is the source point of the arrhythmia is sought. Coagulation of the arrhythmogenic tissue is then effected at this location with radio-frequency or d.c. current, causing the arrhythmogenic tissue to be necrotized. This method is successful in over 90% of cases.

Locating the arrhythmogenic tissue location represents a difficulty in ablation therapy. An endocardial mapping is currently standard, whereby the inside heart wall is scanned with electrodes located at the catheter tip and the electrograms acquired in this way are recorded. The position of the catheter in the heart is monitored with X-ray fluoroscopy. Disadvantages of this approach are that the patient is exposed to radiation and the position of the catheter in the X-ray exposure can only be identified with coarse accuracy.

A more exact positioning of the catheter is achieved by employing an intracardial position identification system, as disclosed in U.S. Pat. No. 5,391,199. The catheter position can be acquired in this system with an error of less than 1 mm. This intracardial position identification system is composed of a transmitter arranged outside the body with transmission antennas, and reception antennas arranged in the tip of the catheter that are connected to a receiver for the interpretation of the reception signal. Further, the intracardial position identification system uses localizable reference catheters that are secured to anatomically projecting locations, at whose catheter tips reception antennas are likewise respectively arranged. The position of the catheter with respect to the reference catheters is determined from the reception signals measured by the antennas. A repositioning of the catheter at locations that have already been previously sought is also simpler using the intracardial positioning system, and is more exact than X-ray monitoring.

A pre-localization or rough localization of the arrhythmogenic tissue in the heart by body surface potential mapping (BSPM), a multi-channel electrocardiography (ECG measuring method with up to 256 electrodes, has exhibited positive results for shortening the endocardial mapping. This method is disclosed, for example, in articles by Sippens Groenewegen, et al, "Body Surface Mapping of Ectopic Left and Right Ventricular Activation", in Circulation, Vol. 82, No. 3, September 1990, pp. 879–896, and of Giorgi et al., "Body surface isopotential mapping of the entire QRST complex in the Wolff-Parkinson-White syndrome. Correlation with the location of the accessory pathway", in American Heart Journal, Vol. 121, No. 5, May 1991, pp. 1445–1453. The results of pre-localization or rough localization are entered in schematic heart images (Sippens Groenewegen) or in magnetic resonance images as well, as described in the article by H. Bruder et al, "The influence of inhomogeneous volume conductor models on the ECG and the MCG", in Phys. Med. Bio., Vol. 39, 1994, pp. 1949–1968. The entry of the localized arrhythmogenic tissue location in magnetic resonance images assumes the application of a localization method as described, for example, in the article by B. Scholz et al., "Probability Based Dipole Localization and Individual Localization Error Calculation in Biomagnetism", in Proc. 14th Ann. Int. Conf. IEEE, Eng. Med. Biol. Soc., Paris, 1992, pp. 1766–1767. The position of the electrodes is acquired first with an extracorporeal position identification system. The thorax geometry is simulated by modeling with, for example, a boundary element method. The position of the arrhythmogenic substrate is identified from the position of the electrodes, the registered measured signals and the modeled thorax geometry, using a source model and an iterative method (for example, Levenberg-Marquardt algorithm) or a raster method. A transformation between the coordinate system established by the extracorporeal position identification system and the coordinate system in which the magnetic resonance image exists remains to be necessary. After the transformation, the localization result is then entered in the magnetic resonance image. An error on the order of magnitude of 6 through 8 mm due to imprecision in the transformation is a disadvantage of this method. Further, the magnetic resonance image is not the same image that is employed later for displaying the heart catheter.

An expansion of the above-recited method is known by the name of pacemapping wherein an attempt is made to optimally simulate a distribution of potential measured in the presence of the arrhythmia with the assistance of a heartbeat triggered by artificial stimulation. The location of the stimulation at which this succeeds is, with good approximation, the source point of the cardiac arrhythmia, and thus the location to be ablated.

The article by Saxon et al., "Transesophageal Echocardiography During Radio-frequency Catheter Ablation of Ventricular Tachycardia", in American Journal of Cardiology, Vol. 72, Sep. 15, 1993, pp. 658–661, describes the experimental utilization of transesophageal ultrasound images as an alternative method to X-ray imaging in the catheter laboratory. An ultrasound probe is thereby positioned in the esophagus in the immediate proximity of the heart in order to produce ultrasound tomograms of the heart. This method offers the advantage that the catheter position can be more exactly determined in the ultrasound tomogram than in the X-ray image, since tomograms of the heart, rather than only projection images, are thereby available.

The employment of intracardial echo cardiography represents another possibility for improving imaging in the catheterization laboratory, whereby an ultrasound imaging head is directly attached to the ablation catheter, as described in articles by Tardiff et al., "Potential Applications of Intracardiac Echocardiography in Interventional Electrophysiology", in American Heart Journal, Vol. 127, No. 4, Part 2, April 1994, pp. 1090–1094, and by Chu et al., "Radio-frequency Catheter Ablation Guided by Intracardiac Echocardiography", in Circulation, Vol. 89, No. 3, March 1994, pp. 1301–1305. Among the advantages of this method are the possibilities of being able to recognize necroses with the ablation catheter that have already occurred, and enablement of a detailed view of cardial anatomic structures, for example the atrial septum.

SUMMARY OF THE INVENTION

An object of the present invention is to provide an apparatus with which arrhythmogenic tissue to be ablated in the heart can be located non-invasively in an accelerated manner and with reduced exposition to radiation.

This object is achieved in an apparatus having a reference catheter fixable in the heart and fashioned such that its spatial position can be identified by the position acquisition unit, and wherein the localization unit localizes the action currents with respect to the reference catheter.

A significantly more exact allocation of the localization result to the anatomy of the heart is possible due to the localization of the action currents with reference to an anatomically distinctive and known point in the heart. The ablation catheter can be brought with high precision to the location determined by the localization unit because the positions of the electrodes are present in the same coordinate system in which the position of the ablation catheter can subsequently be determined with an intracardial position measuring system, and the need for a calculation of a transformation from the coordinate system of the electrodes into the coordinate system of the imaging method is eliminated. For example, the origin of the coordinate system can be placed at the location of the reference catheter. The direction of a coordinate axis, for example the x-coordinate axis of a rectangular coordinate system, can be defined by the direction of the longitudinal axis of the reference catheter.

In an embodiment a diagnostic ultrasound tomography apparatus with a transesophageal or intracardial ultrasound applicator is connected to the localization unit for the positionally correct marking of the localized action currents in a tomogram, with a localizable transmitter or receiver part belonging to the position acquisition unit being arranged at the ultrasound applicator. The position of the ultrasound applicator is thus also known in the same coordinate system in which the localization is implemented. Imprecisions due to coordinate transformation are avoided; the localization result can be entered into the corresponding tomogram with high precision.

In another embodiment a localizable transmitter or receiver part belonging to the position acquisition unit is arranged at a stimulation catheter. Indicating the precision of the localization with error radii in which the point of the localized heart activity is located with a predetermined probability dependent on the signal-to-noise ratio of the measured ECG data, is known from the aforementioned article by Scholz et al. Using the position acquisition unit, a stimulation catheter can then be guided to the origin of the localized activity in the heart in order to implement pacing at that location. The ECG signal obtained from the pacing is subjected to the same localization method as the ECG signal received from the spontaneous heart activity. The spacing of the localized, stimulated heart activity and the position of the pacing catheter determined from the position acquisition device are calculated. If this spacing becomes greater than the error radius for the precision of the localization determined by the signal-to-noise ratio of the ECG signal, then there is a high probability that the modeling on which the localization is based is inadequate and must be iteratively improved until the calculated spacing is smaller than the error radius. An estimate as to whether the modeling needed for the localization method has ensued with adequate precision can be made in this way.

Further, when the location of the stimulation catheter is acquired with the intracardial position acquisition system, the shift of characteristic points in the measured potential distribution at the body surface, for example the potential minimum, can be placed in relationship to the displacement of the catheter by stimulation at a number of locations. A necessary directional shift for the ablation catheter for achieving the target position can be quantified from this relationship. The necessary shift of the catheter is derived, for example, from the difference between the potential minimums in the potential distributions respectively measured in the presence of arrhythmia and in the presence of stimulation.

DESCRIPTION OF THE PREFERRED EMBODIMENTS

Figure 1:
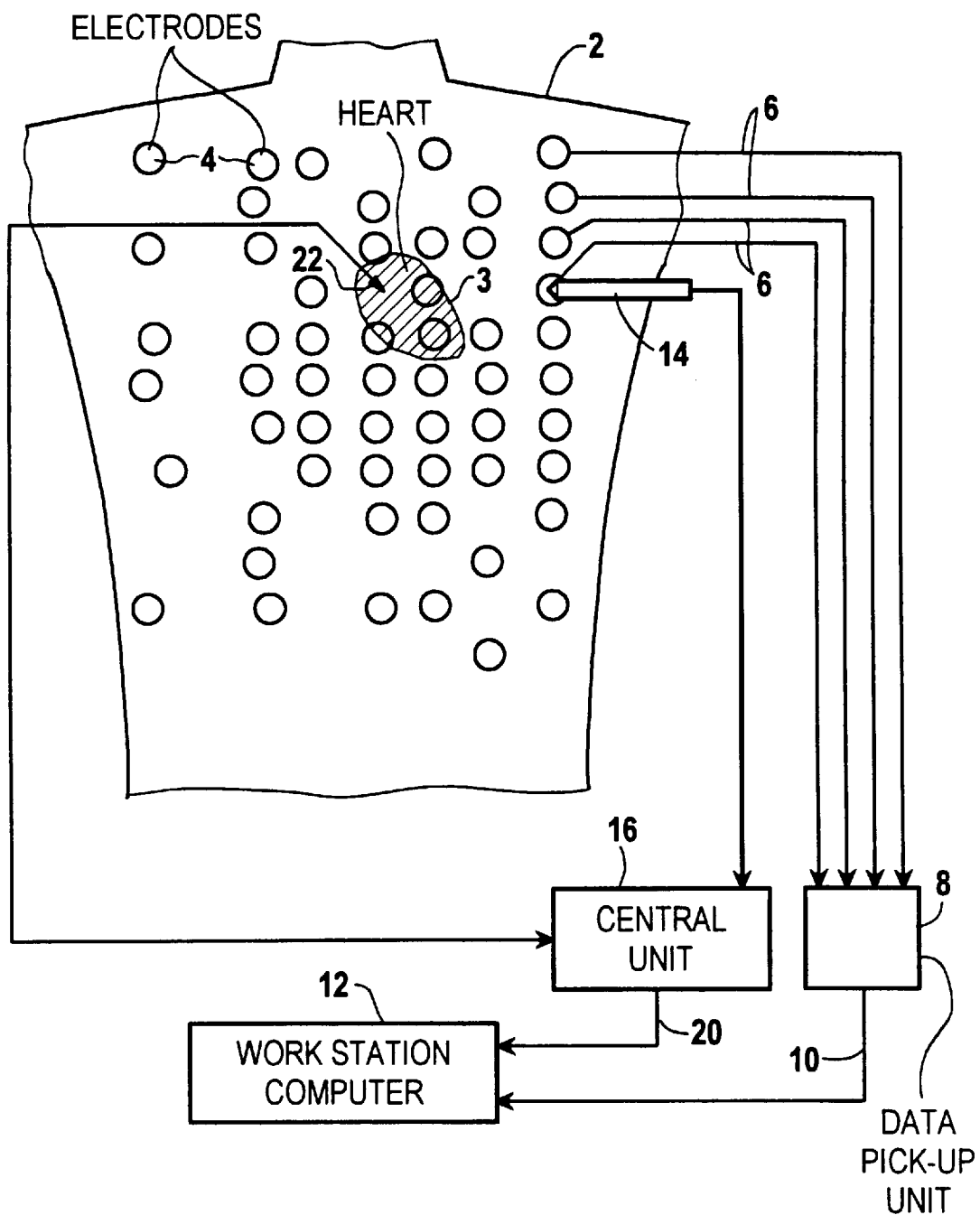
FIG. 1 is a block circuit diagram of an apparatus for localizing action currents with a localizable reference catheter constructed in accordance with the principles of the present invention.

FIG. 1 schematically shows a human torso 2. A shaded region marks the position of the heart 3. Electrodes 4 are adhered to the front and back sides of the torso 2 for deriving potentials on the surface that are generated by heart activities or action currents in order to implement an electrocardiography mapping (ECG mapping). Over 200 electrodes 4 can be employed. Each electrode 4 is connected via a lead 6 to a data pick-up unit 8. For clarity, only a few leads 6 are shown in FIG. 1. The data pick-up unit 8 includes an analog stage with amplifiers as well as analog-to-digital converters for digitizing the measured signals. The digitized measured signals are then communicated via a line 10 to a work station computer 12 fashioned as localization unit.

The spatial position of the electrodes 4 is also needed for the localization of the action currents from the measured potential values. A freely movable unwired pin 14 is provided for this purpose, this pin 14 having an interactive connection to a central unit 16 and forming a position acquisition unit therewith. Such a position acquisition unit is a known device from, for example, Polhemus Inc., USA, that uses magnetic fields in order to acquire a position and an orientation of a location in space. Three coils (not shown) orthogonally arranged in the unwired pin 14 receive a magnetic field emitted by a transmitter. The transmitter is arranged in the central unit 16. The position and orientation of the movable unwired pin 14 in space relative to the stationary central unit 16 is determined from the magnetic field vectors prevailing at the pick-up location and is forwarded via a line 20 to the work station computer 12.

An intracardial receiver, that is arranged at a reference catheter 22 fixable in the heart, is also a component of the position acquisition unit. The reference catheter 22 is fixed at an anatomically distinguished location in the heart 3 and defines the position and the direction of a coordinate system. The localization of the action currents then ensues in this coordinate system, as explained, for example, in the previously cited Scholz et al. article. The localization result can then be entered in anatomical images of the heart, as explained below.

An operation and pacing catheter that can likewise be localized with the assistance of the position acquisition unit can then be positioned at the origin of the localized heart activity. An intracardial mapping now only has to be implemented in the environment of the position prescribed by the localization result, which leads to a saving of operation time and fluoroscopy time in the intracardial mapping.

Figure 2:
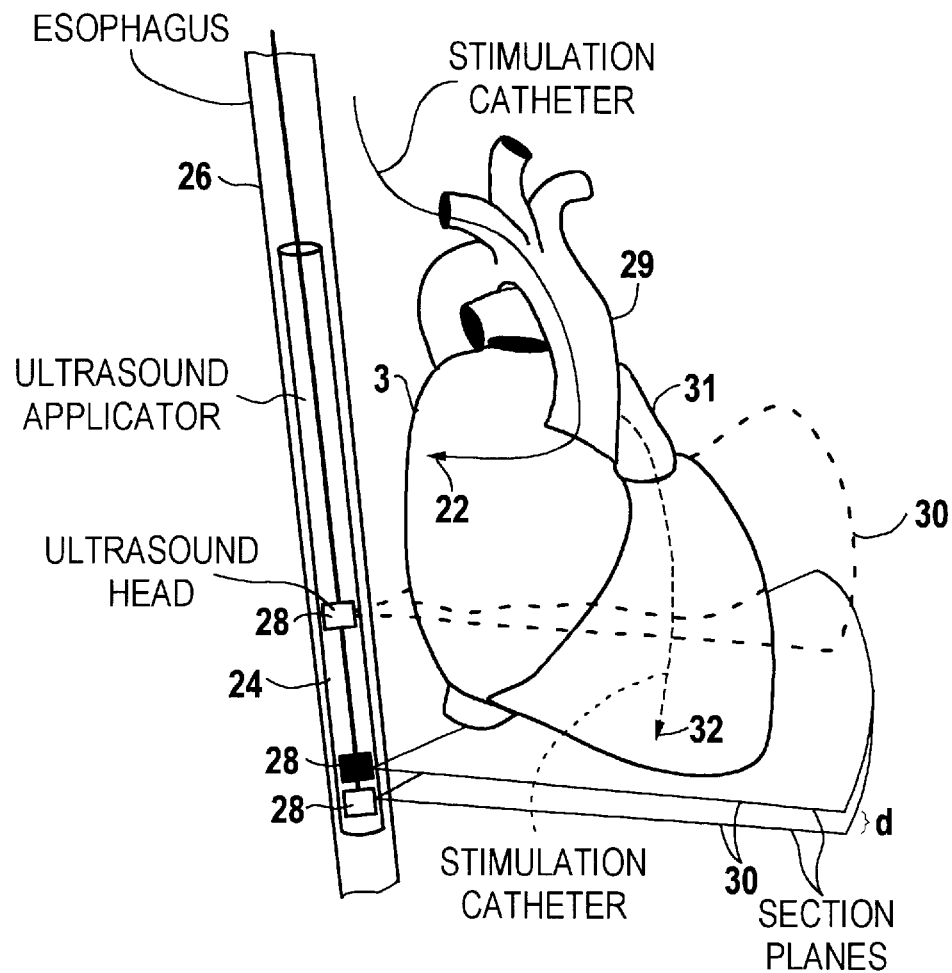
FIG. 2 is a schematic illustration of a transesophageal ultrasound applicator for use in the apparatus of FIG. 1.

FIG. 2 shows a schematic illustration of a transesophageal ultrasound applicator 24 that is positioned in the esophagus 26 in the immediate proximity of the heart 3. An ultrasound head 28, at which a receiver of the position acquisition unit is additionally mounted, is displaceably arranged inside the ultrasound applicator 24. The location of the ultrasound head 28 can thus be identified in the same coordinate system as the electrodes 4, reference catheter 22 and, possibly, the pacing and ablation catheter. The reference catheter 22 is guided into the heart 3 via the arterial outlet and is fixed therein. The ultrasound head 28 is a sector scanner and can produce tomograms of the heart in section planes 30 at, for example, a spacing d of 0.5 mm. Three section planes 30 are shown in FIG. 2 as an example. The position of the arrhythmogenic tissue found from the distribution of potential can then be entered into a corresponding ultrasound tomogram. Instead of a transesophageal applicator 24, the employment of an intracardial applicator is possible, this having a receiver that can be localized by the position acquisition unit.

FIG. 2 also shows a pacing catheter 32 introduced into the heart 3 via the venous outlet 31. The pacing catheter also has a receiver that can be localized by the position acquisition unit. The precision of the localized heart activity can thus be estimated by stimulation. Given deviations that can no longer be tolerated, as set forth above, the model used in the localization is iteratively modified until the error lies in the range of that error caused by the noise of the ECG signal.

The region in which an intracardial mapping must be subsequently carried out is also derived from the estimate of an error radius around the localized heart activity caused by noise. Whether the scanned point still lies in, or already lies outside the error region can be determined at any time using the intracardial position determination system. The region for the endocardial mapping is thus limited, this leading to a shortening of the operation and transirradiation times.

In the above-described position acquisition unit, the transmitter is arranged in the stationary central unit 12 and the receivers are arranged in the unwired pin 14 and the catheters. A position acquisition unit having a number of movable transmitters and a stationary receiver can alternatively be employed, with a respective transmitters being arranged in the unwired pin 14 and in the catheters.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for localizing action currents in a heart of a living subject, comprising:

a plurality of electrodes adapted for attachment to a body surface of a living subject for acquiring a distribution of electrical potential on said body surface generated by cardiac action currents in said subject;

position acquisition means for determining respective spatial positions of said plurality of electrodes;

a reference catheter adapted to be fixed in a heart at a spatial position determinable by said position acquisition means; and localization means connected to said electrodes and to said position acquisition means for localizing said cardiac action currents with reference to said reference catheter using said distribution of electrical potential and the respective spatial positions of said plurality of electrodes.

2. An apparatus as claimed in claim 1 wherein said position acquisition means comprises a central unit and a movable unwired pin connected to said central unit, said central unit including means for localizing said pin.

3. An apparatus as claimed in claim 1 wherein said position acquisition means includes a localizable transmitter disposed at said reference catheter.

4. An apparatus as claimed in claim 1 wherein said position acquisition means includes a localizable transmitter, and said apparatus further comprising diagnostic ultrasound tomography means, having a transesophageal ultrasound applicator, for producing an ultrasound tomogram having a positionally correct marking of a localized action current therein, said transmitter being disposed at said transesophageal ultrasound applicator.

5. An apparatus as claimed in claim 1 wherein said position acquisition means includes a localizable transmitter, and said apparatus further comprising diagnostic ultrasound tomography means, having a intracardial ultrasound applicator, for producing an ultrasound tomogram having a positionally correct marking of a localized action current therein, said transmitter being disposed at said intracardial ultrasound applicator.

6. An apparatus as claimed in claim 1 wherein said position acquisition means includes a localizable transmitter, and said apparatus further comprising means for stimulating said heart using a stimulation catheter, and wherein said transmitter is disposed at said stimulation catheter.

7. An apparatus as claimed in claim 1 wherein said position acquisition means includes a localizable receiver disposed at said reference catheter.

8. An apparatus as claimed in claim 1 wherein said position acquisition means includes a localizable receiver, and said apparatus further comprising diagnostic ultrasound tomography means, having a transesophageal ultrasound applicator, for producing an ultrasound tomogram having a positionally correct marking of a localized action-current therein, said receiver being disposed at said transesophageal ultrasound applicator.

9. An apparatus as claimed in claim 1 wherein said position acquisition means includes a localizable receiver, and said apparatus further comprising diagnostic ultrasound tomography means, having a intracardial ultrasound applicator, for producing an ultrasound tomogram having a positionally correct marking of a localized action current therein, said receiver being disposed at said intracardial ultrasound applicator.

10. An apparatus as claimed in claim 1 wherein said position acquisition means includes a localizable receiver, and said apparatus further comprising means for stimulating said heart using a stimulation catheter, and wherein said receiver is disposed at said stimulation catheter.

* * * * *